United States Patent [19]

Bauer et al.

[11] Patent Number: 5,861,533
[45] Date of Patent: Jan. 19, 1999

[54] PROCESS FOR NITROSATION OF C-H-ACIDIC COMPOUNDS

[75] Inventors: Frank Bauer; Marcel Feld, both of Cologne, Germany

[73] Assignee: Huels Aktiengesellschaft, Marl, Germany

[21] Appl. No.: 869,995

[22] Filed: Jun. 5, 1997

[30] Foreign Application Priority Data

Jun. 5, 1996 [DE] Germany .......................... 196 22 467.5

[51] Int. Cl.⁶ .................................................. C07C 209/38
[52] U.S. Cl. .......................... 564/258; 564/260; 564/253; 564/254; 564/255; 564/256; 564/416; 564/418; 558/443; 560/168
[58] Field of Search ..................... 564/258, 260, 564/253, 254, 255, 256; 558/443; 560/168

[56] References Cited

FOREIGN PATENT DOCUMENTS

| 0 174 519 | 3/1986 | European Pat. Off. . |
| 0 483 674 | 5/1992 | European Pat. Off. . |
| 954 873 | 12/1956 | Germany . |
| 2 352 706 | 4/1974 | Germany . |

OTHER PUBLICATIONS

Patent Abstracts of Japan, vol. 10, No. 239 (C–367), Aug. 19, 1986, JP 61–072741, Apr. 14, 1986.

*Primary Examiner*—Brian M. Burn
*Attorney, Agent, or Firm*—Oblon, Spivak, McClelland, Maier & Neustadt, P.C.

[57] ABSTRACT

A process for nitrosating C-H-acidic compounds. The process substantially avoids producing polluted wastewater.

18 Claims, No Drawings

PROCESS FOR NITROSATION OF C-H-ACIDIC COMPOUNDS

BACKGROUND OF THE INVENTION

1. Field of the Invention

The present invention relates to a process for nitrosating compounds containing an active hydrogen bonded to a carbon atom.

2. Description of the Background

Nitrosation products of C-H-acidic compounds are used as intermediates in the preparation of the corresponding amines, which are, in turn, useful in synthesizing a variety of pharmaceuticals and active agents for plant protection products. Hydroxyimino and nitroso compounds of malonic acid derivatives are examples of these nitrosation products. Many processes for nitrosation of malonic acid derivatives, such as esters, amides, imidoesters and malononitrile, are known. For example, J. B. Paine III et al., in *J Org. Chem.*, 50 (1985), 5598–5604, describe a process for preparing diethyl hydroxyiminomalonate by slowly adding an aqueous solution of sodium nitrite to a solution of diethyl malonate in glacial acetic acid, adding sodium hydroxide solution to the homogeneous reaction mixture, followed by separating the reaction product from the aqueous phase by extraction with diethyl ether. This process produces an aqueous solution containing sodium acetate in approximately 4 times the molar amount of the diethyl malonate.

In German Offenlegungsschrift 23 52 706, ethyl cyanoacetate is first converted to diethyl monoimidomalonate hydrochloride with hydrogen chloride in absolute alcohol, and then the hydrochloride is dissolved in acetic acid. To this solution is added, gradually, an aqueous solution of sodium nitrite, and, at the end of the nitrosation reaction, water is added to the reaction mixture. The reaction product is separated by solvent extraction of the aqueous phase, which contains the sodium acetate by-product of the formation of nitrous acid.

EP-A1-0 517 041 discloses preparing dimethyl hydroxyiminomalonate by adding sodium nitrite and acetic acid to a mixture of dimethyl malonate and water. The reaction mixture is extracted twice using dichloroethane in order to separate the diethyl hydroxyiminomalonate from the sodium acetate, which remains in the aqueous phase. Although sodium nitrite is used only in amounts of 1.2 mol per mole of malonate, the reaction time of 21 hours makes this reaction virtually unusable as an industrial process. Furthermore, the process is unsuitable for reacting malonates of low water solubility.

All of the processes discussed above produce sodium acetate in the form of impure aqueous solutions, which are difficult to dispose of. These processes are, therefore, ecologically unsuitable on an industrial scale.

DE 954 873 describes a process for the preparation of diethyl hydroxyiminomalonate by dissolving diethyl malonate in a solvent, such as toluene, which is not discernibly miscible with water and can be separated from the end product by distillation. To this solution, at least molar amounts of sodium nitrite and from 1 to 10 percent by weight, based on the malonate, of water are added, followed by gradual addition of acetic acid to the suspension at 30° to 70° C. When the nitrosation is finished, the undissolved sodium acetate is separated from the reaction solution and crystallized diethyl hydroxyiminomalonate is obtained from the filtered solution. This process requires no solvent extraction, and indeed about ⅔ of the sodium acetate is obtained in solid form. The process claims to give "smooth and fast reactions and good yields". The latter, at least, is not correct, because the resulting crystalline product having a melting point of 86.5°–88° C. was not diethyl hydroxyiminomalonate, but instead, a complex with sodium acetate. This nitrosation product is so impure that hydrogenation to diethyl acetaminomalonate on platinum catalysts in acetic anhydride, a preferred solvent, is not possible.

Accordingly, there remains a need for a method of nitrosating C-H-acidic compounds that avoids these disadvantages and provides reaction products that can be converted to the corresponding amines.

OBJECTS OF THE INVENTION

It is an object of the present invention to provide a process for converting C-H-acidic compounds to the corresponding hydroxyimino or nitroso derivatives which provides highly pure products in high yield with short reaction times and substantially or even completely avoids producing polluted wastewater.

SUMMARY OF THE INVENTION

The above objects and others are accomplished with a process for nitrosating a compound containing an active hydrogen by contacting a cation-containing niitrite salt with a protic acid in the presence of water to produce nitrous acid and a salt of the cation from the nitrite salt and the conjugate base of the protic acid, followed by nitrosating a compound of formula (I):

$$X^1\text{—CHR—}X^2 \qquad (I),$$

where $X^1$ and $X^2$ are each electron-withdrawing groups. and R is hydrogen or an organic radical.

where the nitrosation reaction occurs in a homogenous liquid phase containing the compound of formula (I), the nitrosation product of the compound of formula (I), water, at least a portion of the nitrite salt and at least a portion of the protic acid, and not less than 50% by weight of the cation-conjugate base salt precipitates from the reaction mixture.

A more complete appreciation of the invention and many of the attendant advantages thereof will be readily obtained as the same becomes better understood by reference to the following detailed description.

DETAILED DESCRIPTION OF THE INVENTION

In the preferred C-H-acidic compounds, i.e., compounds that contain at least one active hydrogen bonded to a carbon atom, of the general formula (I), R is hydrogen. In this case, the nitrosation products are formed not as nitroso compounds but as the tautomeric hydroxyimino compounds, see J. March, *Advanced Organic Chemistry, Reactions, Mechanisms, and Structure*, Fourth Edition, John Wiley and Sons, 1992, pp. 592–593, incorporated herein by reference. If the protic acid, which liberates nitrous acid from the nitrite salt, is a carboxylic acid, the corresponding O-acylated hydroxyimino compounds may also form in variable amounts. The nitrosation products, therefore, may comprise the group  in which R' is hydrogen or an acyl radical derived from the carboxylic acid.

R may also be a organic radical. The organic radical is preferably inert to reaction with any of the components of the present process, such as nitrite salts, protic acids, nitrous acid and water. Preferably, R is a hydrocarbon group containing 1 to 20 carbon atoms. The hydrocarbon group may have any structure. such as linear, branched or cyclic. More preferably, R is an aliphatic or aromatic radical. Most preferably, R is an alkyl radical having 1 to 4 carbon atoms or an aromatic radical having 6 to 10 carbon atoms.

The electron-withdrawing groups $X^1$ and $X^2$ may be the same or different. $X^1$ and $X^2$ are preferably —COOR, —C(NR)OR, —CON(R)$_2$, —COR, —CN, —NO$_2$ or an aromatic radical which may optionally be substituted with inert groups or atoms. In these electron-withdrawing groups, R is as defined above. Preferred aromatic radicals have 6 to 10 carbon atoms which may be substituted by inert groups or atoms. Non-limiting examples of the C-H-acidic compounds of formula (I) include malonic acid and its esters and imidoesters (such as dimethyl malonate, dimethyl 2-methylmalonate, diethyl malonate, diethyl 2-phenylmalonate, diisobutyl malonate, di-2-ethylhexyl malonate and diethyl monoimidomalonate); malonic acid amides and amide esters (such as malonamide, N,N'-dimethylmalonamide, N,N,N',N'-tetra-methylmalonamide and ethyl N,N-dimethylamidomalonate); malononitrile; cyanoacetic acid and its esters (such as ethyl cyanoacetate); 2-cyano-propionic acid and its esters (such as ethyl 2-cyanopropionate); β-keto acids and their derivatives (such as acetoacetic acid and benzoylacetic acid and their esters and amides, for example ethyl acetoacetate, N,N-dimethylacetoacetamide and ethyl benzoylacetate); 1,3-diketones (such as acetylacetone, benzoylacetone and dibenzoylmethane); nitro compounds (such as dinitromethane, ethyl nitroacetate and nitroacetonitrile); aromatic compounds having a further electron-withdrawing group adjoining the —CHR— group (such as phenylacetic acid esters, phenylacetonitrile (benzyl cyanide) and p-nitrophenylacetonitrile).

The nitrosating agent in the present process is presumably nitrous acid, which is liberated in situ from the nitrite salt by the protic acid in the presence of water. The nitrite include alkali metal nitrites, such as sodium and potassium nitrite. The nitrite salt is preferably used in amounts up to 3 mole per mole of C-H-acidic compound (I), more preferably from 1 to 1.5 mol, and most preferably from 1.05 to 1.2 mol per mole of compound (I).

Any inorganic or organic protic acid which is able to at least partially protonate the nitrite salt to form the nitrous acid is suitable in the present process. Preferable inorganic acids include hydrochloric, sulfuric, nitric and phosphoric acids. Carboxylic acids are the preferred organic acids. Non-limiting examples of organic acids include formic acid, acetic acid and propionic acid. Sulfuric acid and acetic acid are particularly preferred. It is advantageous to use the acid in at least the stoichiometric amount corresponding to the nitrite salt. Larger amounts of acid are not harmful, and larger amounts of carboxylic acid are particularly recommended when the nitrosation product is subsequently hydrogenated to the corresponding amine without separation or purification. The acid may also be completely or partially replaced by an acid anhydride. This is particularly advantageous when the C-H-acidic compound and/or its nitrosation product is not highly soluble in water, or in reaction mixtures comprising high proportions of water. The acid anhydride scavenges the water which is formed in the nitrosation reaction, so that the reaction mixture does not accumulate water to an undesirable extent. Naturally, the acid anhydride should not be present in such large amounts that it consumes the added water as well because the solubility of the nitrite salt in the reaction medium would be too low to provide a useful reaction rate.

Formation of nitrous acid from the nitrite salt and the protic acid produces a salt by-product comprising the cation from the nitrite salt and the conjugate base of the protic acid. For, example, sodium acetate is produced when sodium nitrite and acetic acid are used. Sodium sulfate is produced from sodium nitrite and sulfuric acid. The major portion of this salt by-product precipitates from the nitrosation reaction mixture, as discussed below.

Water is an important component of the reaction mixture, since it enables and promotes the liberation of nitrous acid from the nitrite salt. A certain minimum amount of water should be present in order that conversion is as complete and as fast as possible at temperatures which are not excessively high. If less water is used, then a part of the nitrite salt may remain unconverted and make the disposal or re-use of the salt by-product which is formed in the reaction more difficult. On the other hand, the water should be present in the smallest possible amount, particularly when the C-H-acidic compound and/or its nitrosation product have low water solubility. In general, these requirements may be met by using from 0.01 to 50, preferably 0.03 to 20 percent by weight of water, based on the inert organic solvent or solvent mixture which is at least partially miscible with water. The use of a solvent or solvent mixture of this type is an important characteristic of the novel process. It allows nitrosation of C-H-acidic compounds which have low water solubility, such as esters of malonic acid, esters of β-ketoacids and β-diketones. The solvent or solvent mixture contributes to the formation of a homogeneous liquid phase, in which all constituents of the reaction mixture are represented, in which the nitrosation reaction takes place and out of which the salt formed in the nitrosation reaction to a large extent precipitates. It is not necessary for all of the nitrite salt to be present in solution in the homogeneous phase. It is sufficient if a part of it is dissolved, so that an amount of nitrous acid which is sufficient for a fast reaction can be liberated, while the remaining part remains suspended and gradually goes into solution at the rate at which the dissolved nitrite salt is consumed in the nitrosation reaction. This condition is fulfilled by using the amounts of water disclosed above. The amount of the protic acid dissolved in the reaction medium, i.e., in the homogeneous liquid phase, which liberates the nitrous acid from the nitrite salt must naturally correspond at least to the amount of dissolved nitrite salt. Since, however, the protic acid is in generally more soluble in the reaction mixture than is the nitrite salt, this presents no difficulties. In fact, the protic acid is preferably completely dissolved in the aqueous phase. This naturally applies, in particular, for the embodiments described below in which the acid is metered in, but also when the protic acid is part of the initial charge.

For the purposes of the present process, the organic solvents at least partially miscible with water are preferably those which at ambient temperature can dissolve at least 1 percent by weight, more preferably at least 3 percent by weight and, most preferably, more than 5 percent by weight of water. In a particularly preferred embodiment, the organic solvent is miscible in all proportions with water and forms a homogeneous solution. Solvent mixtures are also suitable as long as the mixture dissolves the minimum amount of water discussed above. It is possible, therefore, to work with a solvent mixture containing one solvent which does not dissolve any discernible amount of water and another solvent in which water is highly soluble or which is highly miscible in water, as long as this mixture dissolves water in the stated minimum amounts. The inert organic solvent or solvent mixture is preferably employed in amounts of from 0.05 to 2.5 parts by weight, more preferably from 0.35 to 2.0 parts by weight per part by weight of C-H-acidic compound. Of course, larger amounts of inert organic solvent or solvent mixture can also be used, but this may reduce the space-time yield.

Suitable inert organic solvents include, for example, aliphatic or cyclic ethers (such as dibutyl ether, methyl tert-butyl ether, tetrahydrofuran, 1,4-dioxane, dialkoxyalkanes (for example 1,2-dimethoxyethane) and polyethylene glycol ethers); carboxylic acid esters (particularly those derived from carboxylic acids and alcohols each having from 1 to 4 carbon atoms, such as methyl acetate and ethyl acetate); and N,N-disubstituted carboxylic acid amides (particularly those derived from carboxylic acids having from 1 to 4 carbon atoms, such as N,N-dimehylformamide and N,N-dimethylacetamide); and nitriles (such as acetonitrile and propionitrile). A particularly preferred solvent is 1,4-dioxane. If an organic acid, such as formic acid, acetic acid or propionic acid, is used to liberate the nitrous acid, this acid can serve simultaneously as the inert solvent and the protic acid. This is possible provided that the amounts of the organic acid and the other constituents of the reaction mixture are selected so that, on the one hand, the nitrosation reaction proceeds in a homogeneous phase and, on the other hand, at least the largest part of the salt formed during liberation of the nitrous acid precipitates.

The relative amounts of the inert organic solvent or solvent mixture at least partially miscible with water and water are adjusted such that a homogeneous liquid phase forms as a reaction medium, which completely dissolves the C-H-acidic compound and its nitrosation product and partially dissolves and the nitrite salt and the protic acid. In addition, at least the greatest part, i.e, not less than 50% by weight, preferably at least 60 percent by weight and in particular at least 80 percent by weight, of the salt by-product of the nitrosation reaction is precipitated in solid form. Determining the relative amounts of water and inert solvent is well within the ability of one of ordinary skill in the art. In any case, the major portion of the salt by-product should precipitate, and not be produced as aqueous solution.

The novel process is preferably conducted in the temperature range of 0° to 100° C. It is particularly advantageous to work in the range from 20° to 60° C., more particularly from 30° to 40° C. Below 0° C., the reaction proceeds very slowly. Above 100° C., decomposition occurs and/or byproducts form. It is preferable to increase the temperature toward the end of the reaction, within the stated ranges, in order to complete the conversion. Operation at atomospheric pressure is preferred. Higher pressures may be preferred at higher reaction temperatures or when using low-boiling inert organic solvents, such as methyl acetate, so that these solvents does not escape from the reaction vessel.

To carry out the novel process, the inert organic solvent (if present), the water, the nitrite salt and the C-H-acidic compound may be charged to a stirred reactor and the protic acid which liberates the nitrous acid gradually added. Alternatively, the C-H-acidic compound, the inert organic solvent (if present), water and the protic acid can be charged and the nitrite salt gradually added. This method of operation is preferred when a carboxylic acid simultaneously functions as the protic acid and the inert organic solvent. In both variations it is possible to omit the water from the initial charge and, instead, feed it gradually and separately or together with the acid and/or the nitrite salt. Finally, it is also possible to precharge all of the reaction components except the water, and then add the water gradually. As discussed above, the protic acid can be at least partially substituted by an anhydride so that the water content of the reaction phase does not rise undesirably. This is particularly true when the acid is not precharged but rather is added gradually.

In all the embodiments described above, cooling is applied if desired, in order to maintain the desired reaction temperature. The reaction time depends, in part, on the type of C-H-acidic compound, the reaction temperature and the cooling capacity. It is expedient to increase the temperature by from 10° to 20° C. toward the end of the addition of the acid and to continue the reaction at this temperature. By this means, the last residues of nitrite salt are decomposed, so that the precipitated salt by-product is free from the nitrite salt, and any remaining nitrous gases are driven out of the reaction mixture. This can be achieved, inter alia, by passing an inert gas (such as nitrogen) through the reaction mixture. At the preferred temperatures of from 20° to 60° C., the reaction requires, in general, up to approximately 2 hours.

The lower the water content in the reaction mixture, the smaller the amount of salt by-product that remains dissolved in the reaction mixture. It is possible to reduce the water content of the reaction mixture after nitrosation, for example, by adding an anhydrous salt which takes on water of crystallization. Generally, this also improves the filterability of the precipitated salt. Anhydrous sodium acetate or sodium sulfate are preferred. It is particularly preferred to isolate the sodium acetate or sodium sulfate which forms as the by-product of the present process, dehydrate it by heating at 100° to 200° C. and use this dehydrated salt to remove water from the reaction mixture after nitrosation. In so doing, the salt by-product of the invention process is recycled and reused. Water may, of course, also be removed from the reaction mixture by distilling or stripping it off at the end of the reaction.

In many cases, it may be advantageous to dilute the reaction mixture before separating the precipitated salt by-product with a solvent that is as non-polar and inert as possible. Preferred solvents are ethers or hydrocarbons. Particularly preferred solvents include, for example, such as methyl tert-butyl ether, cyclooctane or isooctane. The reaction mixture can then be more easily manipulated and the salt is more easily filtered off. Furthermore, it has been found that this gives the nitrosation product in a purer form, so that the catalyst requirement in the subsequent catalytic hydrogenation which frequently follows is reduced. Reaction conditions for catalytic hydrogenation are well-known, see, for example, H. O. House, *Modern Synthetic Reactions*, Second Edition, Benjamin/Cummings Publishing Co., 1972, pp. 1–34 and F. A. Carey and R. J. Sundberg, *Advanced Organic Chemistry, Part B: Reactions and Synthesis*, Third Edition, Plenum Press, 1990, pp. 219–232, both incorporated herein by reference. Platinum catalysts are preferred.

Even without dilution of the reaction mixture, the salt by-product can be isolated with remarkable purity and, after washing with a suitable solvent (such as methyl tert-butyl ether, cyclohexane or ethyl acetate), and after drying, can be employed in other processes. In the novel process, salt solutions which are difficult to dispose of are produced in, at most, minor amounts.

Having generally described this invention, a further understanding can be obtained by reference to certain specific examples which are provided herein for purposes of illustration only and are not intended to be limiting unless otherwise specified.

EXAMPLES

Example 1

112.2 g of acetic acid (96%; 1.8 mol) were added dropwise over 2 hours to a stirred mixture of 120.0 g (1.0 mol)

of dimethyl malonate, 250.0 g of 1,4-dioxane, 35.6 g of water and 80.0 g (1.15 mol) of sodium nitrite (technical grade), maintained at from 35° to 40° C. The reaction was allowed to continue for 2 hours at 50° C., then 35 g of anhydrous sodium acetate and 400 g of methyl tert-butyl ether were added. After cooling to ambient temperature, the precipitated coarsely crystalline solid was filtered off using suction and was washed twice using 150 ml of methyl tert-butvl ether each time. The filtrate and the wash liquid were freed from low-boilers at 60° C. under water pump vacuum. This gave 186.4 g of a solid residue melting in the range from 47° to 56° C. Analysis by gas chromatography/mass spectroscopy (GC/MS) showed a mixture of dimethyl hydroxyiminomalonate and dimethyl acetoxyiminomalonate. By GC analysis the product contained <0.5 FID area percent of unconverted dimethyl malonate.

Example 2

224.3 g (3.6 mol) of acetic acid were added dropwise over 2 hours to a mixture of 320.4 g (2.0 mol) of diethyl malonate, 500 g of 1,4-dioxane, 71.2 g of deionized water and 160 g (2.3 mol) of sodium nitrite (technical grade), maintained at 40° C. The reaction mixture was allowed to continue reacting for 1 hour at 50° C., was cooled to ambient temperature and the homogeneous mixture was seeded with sufficient sodium acetate trihydrate to cover the tip of a spatula, upon which the sodium acetate formed during the reaction precipitated in coarsely crystalline form comprising from 0 to 3 molecules of water of crystallization. The mixture was filtered, the filter cake washed using 1,4-dioxane, and the low boilers were distilled off from the filtrate and from the wash liquid. There remained 423.0 g of a clear, light yellow oil, containing <0.6 FID area percent of unconverted diethyl malonate. Catalytic hydrogenation and recrystallization of the crude product gave diethyl acetaminomalonate in a yield of 85% of theory, based on diethyl malonate employed, with a purity of >99.8 FID area percent.

Example 3

The procedure of Example 2 was followed, however after the end of the reaction 70 g of anhydrous sodium acetate (obtained from a previous reaction mixture by filtration and drying at 130° C. under water-pump vacuum) were added. By this method, the sodium acetate formed could be filtered off more easily than in Example 2, the yield was 417.2 g of light yellow oil comprising <0.6 FID area percent of unconverted diethyl malonate. Catalytic hydrogenation and recrystallization of the crude product gave diethyl acetamidomalonate at a yield of 85% of theory, based on the diethyl malonate employed, and a purity of >99.8 FID area percent.

Example 4

The procedure of Example 3 was followed, but after addition of the anhydrous sodium acetate 400 g of methyl tert-butyl ether was also added. 426 g of light yellow oil remained, which gave, on catalytic hydrogenation and recrystallization of the crude product, diethylacetamidomalonate at a yield of 88% of theory, based on the diethyl malonate employed, and with a purity of >99.8 FID area percent.

Example 5

A mixture of 1,4-dioxane, acetic acid and water, obtained from a previous reaction mixture by taking a low-boiling cut, was metered into a stirred mixture of 320.4 g (2.0 mol) of diethyl malonate and 160 g (2.3 mol) of sodium nitrite (technical grade), maintained at 35° C. 12.0 g of water were then metered in and 166 g (207. mol) of acetic acid (96%) were added dropwise over 2 hours. The mixture was allowed to continue reacting for 2 hours at 40° C. and was worked up as described in Example 4. There remained 425 g of light yellow oil, which, after catalytic hydrogenation and recrystallization of the crude product, gave diethyl acetaminomalonate at a yield of 86% of theory, based on the diethyl malonate employed, and with a purity of >99.8 FID area percent.

Example 6

The procedure of Example 2 was followed, but the 1,4-dioxane was replaced by tetrahydrofuran. There remained 427 g of light yellow oil, which comprised <1 FID area percent of unconverted diethyl malonate.

Example 7

The procedure of Example 3 was followed, however the 1,4-dioxane was replaced by 600 g of ethyl acetate, the amount of water added was reduced to 20 g and the acetic acid was replaced by 166.6 g of acetic anhydride. There remained 425 g of light yellow oil, which, after catalytic hydrogenation and recrystallization of the crude product, gave diethyl acetaminomalonate in a yield of 85% of theory, based on the diethyl malonate employed, and with a purity of >99 FID area percent.

Example 8

The procedure of Example 3 was followed, but the 1,4-dioxane was replaced by the same amount of polyethylene glycol ether (molecular weight about 500). This gave 921 g of a solution comprising the nitrosation products. It comprised <1 FID area percent of unconverted diethyl malonate.

Example 9

112.2 of acetic acid (96%) were added dropwise over 2 hours to a stirred mixture of 216.0 g (1 mol) of diisobutyl malonate, 250 g of 1,4-dioxane, 25.6 g of deionized water ad 80 g (1.15 mol) of sodium nitrite (technical grade), maintained at from 35° to 40° C. The mixture was allowed to continue reacting for 2 hours at 50° C., then 35.0 g of anhydrous sodium acetate and 200 g of methyl tert-butyl ether were added. After cooling of the mixture, the precipitated coarsely-crystalline sodium acetate trihydrate was filtered off and washed using methyl tert-butyl ether. Removal of the low-boilers by distillation at 60° C. under water-pump vacuum gave 258.7 g (88.6% of theory) of residue comprising primarily diisobutyl hydroxyiminomalonate. The content of unconverted diisobutyl malonate was 0.4 FID aea percent.

Example 10

570.0 g of concentrated sulfuric acid was added dropwise over 2 hours to a stirred mixture of 113.1 g (1.0 mol) of ethyl cyanoacetate, 250.0 g of 1,4-dioxane, 35.6 g of deionized water and 80.0 g (1.15 mol) of sodium nitrite (technical grade), maintained at 25° C. The mixture was allowed to continue reacting for 2 hours at 25° C., then 400 g of methyl tert-butyl ether were added, the mixture was cooled to ambient temperature, and the suspension obtained was filtered. The filter cake was washed twice using 100 ml of methyl tert-butyl ether each time. Low-boilers were removed from the filtrate and the wash liquid at 60° C./16 mm Hg. There remained 136.7 g of oily crystalline residue comprising <0.4 FID area percent of unconverted ethyl cyanoacetate.

Example 11

112.2 g of acetic acid (96%; 1.8 mol) were added dropwise over 2 hours to a stirred mixture of 130.2 g of ethyl acetoacetate, 250 g of 1,4-dioxane, 35.6 g of deionized water and 80 g of sodium nitrite, maintained at 35° C. The mixture was allowed to continue reacting for 2 hours at 50° C., 200 g of methyl tert-butyl ether were added to the clear solution obtained and the mixture was cooled to ambient temperature. After filtering off and washing the precipitated solid, the filtrate and the wash liquid were concentrated at 60° C. under water-pump vacuum. There remained 170.4 g (99% of theory) of ethyl acetoxyiminoacetoacetate comprising 0.5 FID area percent of unconverted ethyl acetoacetate.

Example 12

112.2 g of acetic acid (96%; 1.8 mol) were metered in over 2 hours to a stirred mixture of 224.0 g of dibenzoylmethane, 250 g of 1,4-dioxane, 35.6 g of deionized water and 80.0 g of sodium nitrite (technical grade), maintained at 35° C. The mixture was allowed to continue reacting for 2 hours at or below 40° C., 600 g of methyl tert-butyl ether was added and the mixture cooled to ambient temperature. After filtering off and washing the precipitated sodium acetate, the filtrate and the wash liquid was freed from low-boilers at 60° C. under water-pump vacuum. There remained 216.6 g of crystalline residue comprising 4 FID area percent of unconverted dibenzoylmethane.

Example 13

28.2 g sulfuric acid was added dropwise over 3 hours to a stirred mixture of 51.0 g of malonamide, 41.8 g of deionized water, 250 g of 1,4-dioxane and 19.9 g of sodium nitrite (technical), maintained at 20° C. The reaction was allowed to continue for 2 hours at 30° C., 300 ml of ethyl acetate, followed by 20.0 g of anhydrous sodium sulfate, were added to the mixture, and it was cooled to ambient temperature. The precipitated solid was filtered off and washed several times using ethyl acetate. The low-boilers were removed from the filtrate and from the wash liquid under reduced pressure. The residue was a nitrosation product having a melting range of from 158° C. to 167° C. and comprising <2 FID area percent of unconverted malonamide.

Example 14

225.0 g of glacial acetic acid were added dropwise over 2 hours to a stirred mixture of 320 g (2 mol) of diethyl malonate, 15 g of deionized water and 160 g (2.3 mol) of sodium nitrite, maintained at 35° C. The reaction was allowed to continue for 2 hours at 50° C., then the mixture was filtered and the filter cake washed with glacial acetic acid. The filtrate and the wash liquid were freed from low-boilers at 60° C. under water-pump vacuum. The residue was 410.1 g of a clear, light yellow oil, which gas-chromatographic analysis showed to contain, in addition to diethyl hydroxyiminomalonate and diethyl O-acetoxyiminomalonate, 5 FID area percent of unconverted diethyl malonate. The separated sodium acetate was dried at 60° C. under water-pump vacuum (final weight 160.0 g). It was fully soluble in deionized water.

Example 15

The procedure of Example 14 was followed, however after the end of the reaction 800 g of methyl tert-butyl ether were added, and the mixture was filtered at ambient temperature. There remained 420.0 g of clear, light yellow oil, which gas-chromatographic analysis showed to comprise, in addition to diethyl hydroxyiminomalonate and diethyl O-acetoxyiminomalonate, 5 FID area percent of unconverted diethyl malonate.

Obviously, numerous modifications and variations of the present invention are possible in light of the above teachings. It is therefore to be understood that within the scope of the appended claims, the invention may be practiced otherwise than as specifically described herein.

The present application is based on German Patent Application No. 196 22 467.5, filed Jun. 5, 1996, and incorporated herein by reference in its entirety.

What is claimed as new and is desired to be secured by Letters Patent of the United States is:

1. A process for nitrosating a compound containing an active hydrogen, comprising:

contacting a nitrite salt comprising a cation and a nitrite ion with a protic acid in the presence of water to produce nitrous acid and a salt comprising the cation and the conjugate base of the protic acid; and nitrosating a compound of formula (I),

$$X^1\text{---}CHR\text{---}X^2 \qquad (I),$$

wherein $X^1$ and $X^2$ are each, independently, an electron-withdrawing group, and R is hydrogen or an organic radical, wherein the nitrosation reaction occurs in a homogenous liquid phase comprising the compound of formula (I), the nitrosation product of the compound of formula (I), water, at least a portion of the nitrite salt and at least a portion of the protic acid, and not less than 50% by weight of the salt comprising the cation and the conjugate base of the protic acid precipitates.

2. The process of claim 1, wherein at least one inert organic solvent which is at least partially miscible with water is used in the contacting step, and the homogeneous liquid phase comprises at least a portion of the inert organic solvent.

3. The process of claim 2, wherein the inert organic solvent comprises an aliphatic or cyclic ether, a carboxylic acid ester or a carboxylic acid amide.

4. The process of claim 2, wherein the inert organic solvent is selected from the group consisting of dibutyl ether, methyl tert-butyl ether, tetrahydrofuran, 1,4-dioxane, 1,2-dimethoxyethane, polyethylene glycol ethers, methyl acetate, ethyl acetate, N.N-dimethylformamide, N,N-dimethylacetamide, acetonitrile and propionitrile.

5. The process of claim 1, wherein $X^1$ and $X^2$ are independently selected from the group consisting of —COOR, —C(NR)OR, —CON(R)$_2$, —COR —CN, —NO$_2$ and an aromatic radical.

6. The process of claim 1, wherein R is hydrogen, an alkyl radical having from 1 to 4 carbon atoms or an aryl radical having from 6 to 10 carbon atoms.

7. The process of claim 1, wherein the nitrite salt is an alkali metal nitrite and is used in an amount of from 1 to 1.5 mol per mole of the compound of formula (I).

8. The process of claim 1, wherein at least a portion of the protic acid is used in the form of its anhydride and in an amount which is at least equivalent to the amount of the nitrite salt.

9. The process of claim 1, wherein the protic acid is acetic acid or sulfuric acid.

10. The process of claim 1, further comprising, after the contacting and nitrosating steps, adding to the reaction mixture a material which absorbs water.

11. The process of claim 1, wherein not less than 60% by weight of the salt comprising the cation and the conjugate base of the protic acid precipitates.

12. The process of claim 1, wherein not less than 80% by weight of the salt comprising the cation and the conjugate base of the protic acid precipitates.

13. The process of claim 1, further comprising, after the contacting and nitrosating steps, removing water from the reaction mixture by distilling or stripping.

14. The process of claim 1, further comprising isolating the nitrosation product of the compound of formula (I), which is substantially free of the salt comprising the cation and the conjugate base of the protic acid.

15. The process of claim 1, further comprising catalytically hydrogenating the nitrosation product of the compound of formula (I) to the corresponding amine.

16. The process of claim 1, further comprising isolating the precipitated salt comprising the cation and the conjugate base of the protic acid.

17. The process of claim 1, which substantially avoids producing polluted wastewater.

18. A process for preparing an amine, comprising:

contacting a nitrite salt comprising a cation and a nitrite ion with a protic acid in the presence of water and to produce nitrous acid and a salt comprising the cation and the conjugate base of the protic acid;

nitrosating a compound of formula (I), $$X^1\text{—CHR—}X^2 \qquad (I),$$

wherein $X^1$ and $X^2$ are each, independently, an electron-withdrawing group, and R is hydrogen or an organic radical, wherein the nitrosation reaction occurs in a homogenous liquid phase comprising the compound of formula (I), the nitrosation product of the compound of formula (I), water, at least a portion of the nitrite salt and at least a portion of the protic acid, and not less than 50% by weight of the salt comprising the cation and the conjugate base of the protic acid precipitates; and catalytically hydrogenating the nitrosation product of the compound of formula (I) to the corresponding amine.

* * * * *